United States Patent
Ratjen

(10) Patent No.: US 11,596,746 B2
(45) Date of Patent: Mar. 7, 2023

(54) MEDICAMENT DELIVERY DEVICE

(71) Applicant: SHL MEDICAL AG, Zug (CH)

(72) Inventor: Jochen Ratjen, Nacka (SE)

(73) Assignee: SHL MEDICAL AG, Zug (CH)

( * ) Notice: Subject to any disclaimer, the term of this patent is extended or adjusted under 35 U.S.C. 154(b) by 364 days.

(21) Appl. No.: 16/712,643

(22) Filed: Dec. 12, 2019

(65) Prior Publication Data

US 2020/0188611 A1 Jun. 18, 2020

(30) Foreign Application Priority Data

Dec. 18, 2018 (EP) .................................... 18213790

(51) Int. Cl.
| | |
|---|---|
| *A61M 5/315* | (2006.01) |
| *A61M 5/19* | (2006.01) |
| *A61M 5/20* | (2006.01) |
| *A61M 5/32* | (2006.01) |
| *A61M 5/36* | (2006.01) |
| *A61M 15/00* | (2006.01) |

(52) U.S. Cl.
CPC ............ *A61M 5/3155* (2013.01); *A61M 5/19* (2013.01); *A61M 5/2033* (2013.01); *A61M 5/3202* (2013.01); *A61M 5/36* (2013.01); *A61M 15/0065* (2013.01); *A61M 2202/064* (2013.01)

(58) Field of Classification Search
CPC .............. A61M 5/36; A61M 2005/314; A61M 5/3202; A61M 5/3155; A61M 5/2033; A61M 2005/2006; A61M 5/19; A61M 5/20; A61M 5/3146
See application file for complete search history.

(56) References Cited

U.S. PATENT DOCUMENTS

| | | | | |
|---|---|---|---|---|
| 1,390,858 | A * | 9/1921 | Amerman ................ | G01N 9/14 73/441 |
| 1,683,452 | A * | 9/1928 | Edelmann ................ | G01N 9/14 73/441 |
| 1,762,237 | A * | 6/1930 | Moore .................... | A61C 17/02 239/327 |
| 3,635,218 | A * | 1/1972 | Ericson ................. | A61M 3/0262 604/38 |
| 4,130,117 | A * | 12/1978 | Van Eck ................ | A61M 5/282 604/200 |
| 4,258,714 | A * | 3/1981 | Leopoldi ............. | A61M 3/0262 D24/115 |
| 4,645,488 | A * | 2/1987 | Matukas ................ | A61M 31/00 604/218 |
| 5,020,694 | A * | 6/1991 | Pettengill ............. | B65D 81/325 401/35 |

(Continued)

FOREIGN PATENT DOCUMENTS

| | | |
|---|---|---|
| EP | 1409046 B1 | 4/2004 |
| WO | 2006/058435 A2 | 6/2006 |

(Continued)

*Primary Examiner* — Theodore J Stigell
(74) *Attorney, Agent, or Firm* — McDonnell Boehnen Hulbert & Berghoff LLP

(57) ABSTRACT

A medicament delivery device is presented having an elongated body having a longitudinal axis, a proximal end and a distal end that is provided with a distal surface. The distal surface is arranged and configured such that the elongated body of the medicament delivery device can steadily stand on the distal surface.

13 Claims, 6 Drawing Sheets

(56) References Cited

U.S. PATENT DOCUMENTS

| | | | | |
|---|---|---|---|---|
| 5,324,273 | A | * | 6/1994 | Discko, Jr. ........... A61C 9/0026 604/311 |
| 5,697,918 | A | * | 12/1997 | Fischer ............... A61M 5/3135 604/235 |
| 5,848,993 | A | * | 12/1998 | Tanhehco ............ A61M 3/0262 D24/115 |
| 8,052,645 | B2 | * | 11/2011 | Slate ....................... A61M 5/20 604/154 |
| 2003/0100866 | A1 | * | 5/2003 | Reynolds .............. B65B 7/2821 29/428 |
| 2004/0116875 | A1 | * | 6/2004 | Fischer ............... A61M 5/3129 604/227 |
| 2005/0261634 | A1 | | 11/2005 | Karlsson |
| 2010/0049125 | A1 | | 2/2010 | James et al. |
| 2010/0241067 | A1 | * | 9/2010 | Magrini ............ A61M 5/31596 604/82 |
| 2017/0072142 | A1 | | 3/2017 | Perthu |
| 2018/0243499 | A1 | | 8/2018 | Visentin |

FOREIGN PATENT DOCUMENTS

| | | |
|---|---|---|
| WO | 2010/003262 A2 | 1/2010 |
| WO | 2016/193622 A1 | 12/2016 |

\* cited by examiner

A2-A2

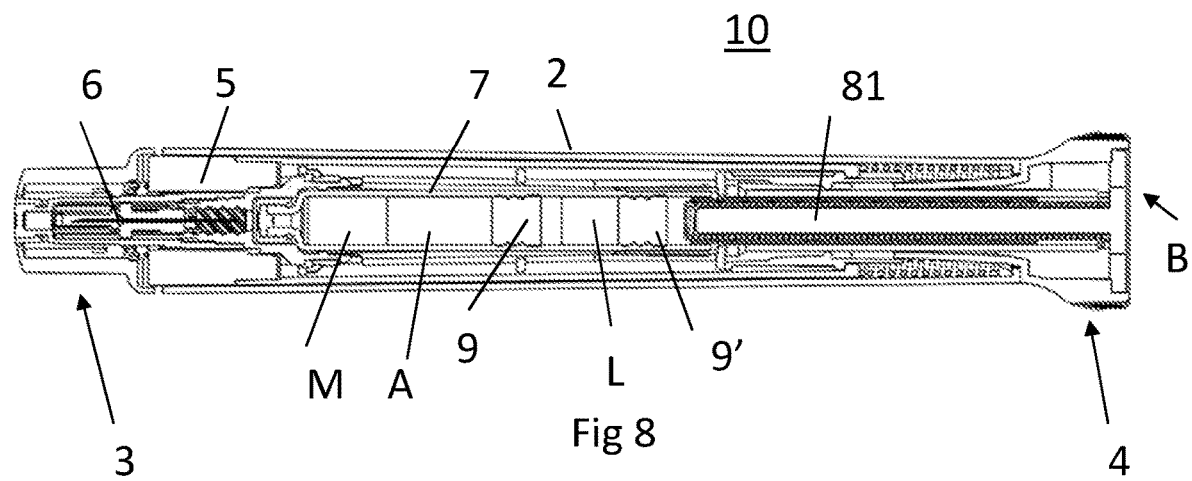
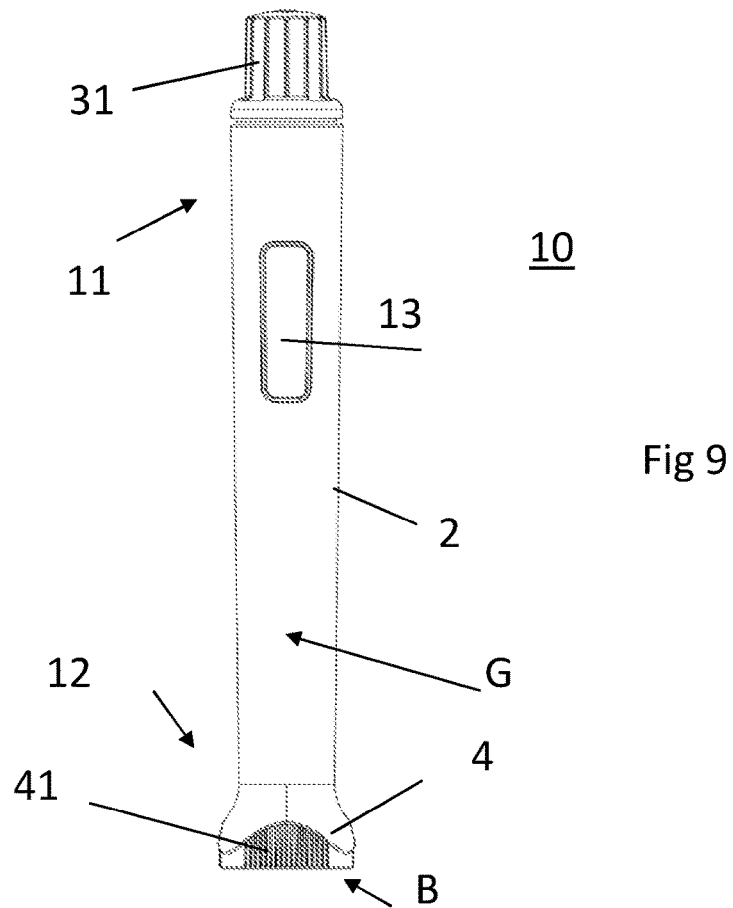

MEDICAMENT DELIVERY DEVICE

CROSS REFERENCE TO RELATED APPLICATION

The present application claims priority to European Patent Application No. 18213790.1 filed Dec. 18, 2018, which is herewith incorporated by reference into the present application.

TECHNICAL AREA

The disclosure relates to a medicament delivery device such an automatic or a manual injector or an inhaler containing a syringe, a container or a cartridge with a medicament and used for self-administration of a medicament.

BACKGROUND

A number of medicament delivery devices for self-administration of medicaments are on the market and different designs had been developed depending on which kind of medicament is to be delivered, which dose etc. Usually it is an elongated portable device held by a user, e.g. a pen-like device. As those devices may contain a fragile parts, e.g. of glass, any fall should be avoided not only due to possible damage to the fragile parts, but also due to hygiene/sterility requirement on the medicament delivery device. The conventional elongated medicament delivery device is usually kept horizontally for natural reasons as, due to the elongated form, it often tends to be unstable in a vertical position and falls easily. Also, such a medicament delivery device is often cylindrical and will easily start to roll on a planar surface. There is thus a risk that the medicament delivery device will roll off a table and be damaged and/or contaminated. Therefore there is a need to prevent an elongated and generally cylindrical medicament delivery device from rolling on planar surfaces.

As the devices are often used for self-administration, it is very important that the dosage of the medicament delivered is correct and that the medicament, which is often expensive, and sometimes hazardous if handled incorrectly, does not get spilled.

Particularly, the problem of accidental expulsion of medicament by an air bubble may occur in so called multi-chamber containers, where one chamber may comprise the medicament as e.g. a powder or as a dried substance, where this chamber also comprises air. A second chamber may comprise a liquid or solvent/diluent or inhibitor or catalyst which is to be mixed with the medicament in the first chamber prior to the delivery of the reconstituted medicament to a patient. Optionally, two different liquid components in two chambers may be mixed prior to delivery.

During the mixing process, especially if mixed quickly, e.g. in automatic or semi-automatic medicament delivery devices where a spring drives the mixing process, a foam, or air bubbles, may form which may disturb the dose delivery. During device activation, e.g. performing an delivery, after setting a dose, if air bubbles are present in the reconstituted medicament, an unpredictable portion of the medicament may be expelled prior to the dose delivery itself so that the actual dosage delivered to a patient is reduced. Even single chamber containers may contain some air which needs to be removed prior to delivery. The process of removing air prior to the injection called priming.

Thus, the accuracy of the dose delivery may be jeopardised due to air bubbles in the medicament to be delivered.

To solve this problem, WO2010/003262 discloses an injection apparatus comprising a safeguard mechanism for assuring complete mixing of medicament in a multi-chamber cartridge prior to injection. The apparatus comprises a metering and/or actuating element and a housing, the metering and/or actuating element only being released by the safeguard mechanism after the mixing of the medicament in the multi-chamber cartridge.

The uncontrolled expulsion of medicament may occur due to air bubbles that tend to escape even in a syringe or a single-chamber cartridge or a container, which may also contain some the air.

WO 2016/193622 discloses another kind of medicament delivery device such as an auto-injector with a single-chamber reservoir. A piston rod is used to cooperate with a piston of the reservoir. The piston rod is moved by an injection spring between a loaded position and an injection position in which latter position said piston rod has moved the piston of the reservoir in order to inject the fluid product into an injection site. The auto-injector comprises a delay system for delaying the end of actuation of an indicator device relative to the end of the injection. The indicator device generates a noise during the actuation of the indicator device.

Some devices solve this problem by first manually priming the device and only then setting the correct dosage to be delivered.

EP1 409 046 discloses a medication dispensing apparatus with a drive mechanism including a plunger that is manually pullable relative to the housing in a proximal direction to shift the apparatus from a ready state to a cocked state, and which is manually pushable relative to the housing in a distal direction to force medicine out through the injection needle while returning the apparatus from the cocked state to the ready state. The apparatus includes a priming mechanism for priming the injection needle with medicine from the reservoir, which priming mechanism includes a drive portion external to the housing to be manually rotatable relative to the housing. The apparatus further includes a rotation controlling mechanism that permits manual rotation of the priming mechanism drive portion in a first direction and as far as necessary to achieve priming, and that prevents manual rotation of the priming mechanism drive portion in a direction opposite to the first direction. Nevertheless, this is rather complicated operation of the device with a number of steps to be remembered and done by an untrained user. Therefore, there is a need to provide a medicament delivery device that is easier to handle for a disabled person and still preventing the medicament from accidental expulsion prior to dose delivery. At the same time there is a need to prevent damage or mismanaging of the medicament delivery device.

SUMMARY

An object of this disclosure is to provide a device that ensures a correct dosage delivered by a medicament delivery device of any kind, e.g. a medicament delivery device in which a dose is pre-set and cannot be varied after priming or a single chamber and/or a multi-chamber device, manually or automatically driven, where correct dosage is achieved by proper priming. The improved novel medicament delivery device according to the disclosure reduces the amount of the preparation steps, simplifies performance and enables self-administration of the medicament for any untrained or physically impaired users. In the present disclosure, when the term "distal" is used, this refers to a direction pointing away from the dose delivery site. When the term "distal part/end" is used, this refers to a part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

The first aspect of the disclosure is a novel design, or a novel shape, of the medicament delivery device allowing the medicament delivery device to be safely placed and kept vertically standing on its rear distal end so that a proximal end of the device and a container with a medicament situated within the medicament delivery device is directed vertically up enabling a proper priming for air evacuation. As known, an air bubble in a liquid will tend to move up. Therefore, when the proximal end of the device, usually equipped with a delivery member such as a needle or discharging nozzle, is directed upwards, the air bubble (e.g. resulting from mixing) will move up and can escape through the delivery member particularly during or after priming without pushing out a portion of the liquid medicament. An automatic, electric or a manual medicament delivery device for self-administration comprises an elongated body with a longitudinal axis, a proximal end and a distal end, which distal end is provided with a distal rear surface. The distal rear surface is arranged substantially perpendicular to the longitudinal axis of the medicament delivery device. The distal end and the distal end base surface are arranged and configured to allow the elongated body of the medicament delivery device to stand steadily on its distal rear base surface, securely supporting the device in its up-right standing position. The elongated body may have a shape, such that a cross-sectional area of the medicament delivery device body, perpendicular to the longitudinal axis at its proximal end, is smaller than a cross-sectional area of the medicament delivery device body at its distal end, thus promoting the steadiness of the medicament delivery device in the vertical position. The vertical position may be advantageous when removing a cap, performing mixing, engaging or connecting a needle shield, attaching a delivery member, at priming etc.

At the same time, or alternatively, a centre of a gravity of the medicament delivery device can be arranged so that the distance along the longitudinal axis of the medicament delivery device from the centre of gravity is shorter to the distal end than to the proximal end of the medicament delivery device, which increases stability of the device having an elongated body and allows smaller dimensional differences in the cross-sectional areas between the proximal and distal ends and yet further ensures the medicament delivery steadiness on its distal rear base surface.

The elongated body of the medicament delivery device may be formed by an outer housing shell. Alternatively, the elongated body of the medicament delivery device may be formed by an outer housing shell and a knob. The knob may have an enlarged cross-sectional area compared to the proximal end and/or the distal end of the outer housing shell. The distal base surface on which the medicament delivery device may stand upright is formed by one of the outer housing shell distal end and the knob. The distal surface of the delivery device may be flat. Alternatively, the distal surface may have an anti-slipping arrangement such as an anti-slipping profile comprising ribs, grooves, extensions, a coarse surface structure or the like, to enhance its friction property against a support surface on which the medicament delivery device is to be placed to stand vertically. Alternatively, a suction cup can be arranged at the distal end for ensuring the device's vertical position on the support surface. The anti-slipping arrangement improves the steadiness of the vertically positioned elongated body on the support surface during performance of any functions requiring, or facilitated by, a vertical positioning of the medicament delivery device.

The anti-slipping arrangement comprises at least one of an anti-slipping material and an anti-slipping surface structure, or profile, to improve the stability of the medicament delivery device in its substantially vertical position when standing on its distal end surface.

The knob may be one of a dose setting knob, a device activating knob, a mixing knob, an unlocking knob and a charging connector knob.

The medicament delivery device may further comprise one of a multi-chamber cartridge or container, a syringe and a single-chamber container or reservoir with a medicament. The medicament delivery device may be of any kind such as one of an automatic, mechanically or electrically driven device having a manually or automatically driven dose-setting mechanism.

The medicament delivery device may further comprise at its proximal end at least one of a removable cap and a needle shield, wherein the substantially vertical position of the medicament delivery device standing on its rear distal surface allows operations such as storage, activation, removing the cap, mixing the medicament, priming the device, operating the needle shield and charging the medicament delivery device, with only one hand.

The medicament delivery device may be one of a pre-set dose device and a variable dose delivery device. The medicament delivery device may be one of a single dose delivery device and a multiple dose delivery device.

The elongated body of the medicament delivery device may be provided with a removable protective cap at its proximal end.

The elongated body of the medicament delivery device may be provided with a window for monitoring a medicament status and/or a delivery status.

The second aspect of the disclosure, where the body shape and/or placement of the gravity centre promotes the steady vertical positioning of the device as explained above, is that when the medicament delivery device accidentally falls from its vertical position, or is just placed horizontally, the elongated body outer shape prevents it from rolling on the surface. The cross-sectional area at the proximal end and the cross-sectional area at the distal end of the medicament delivery device may have the same or the different circumferential shapes and or sizes. At least one of the cross-sectional areas at the proximal and distal ends of the medicament delivery device elongated body has a circumferential shape preventing the rolling of the medicament delivery device when in the horizontal position. As explained above, the medicament delivery device elongated body distal end may have a bigger cross-sectional than the proximal end, and thus the device longitudinal axis will be inclined in relation to the supporting surface on which the medicament delivery device lies in such a case. Thus, those two aspects of the inventive shape of the medicament delivery device elongated body together serve to increase safety in use of the device, ensuring the correct dosage of the medicament due to prevention of medicament expulsion and rolling of the medicament delivery device, which that might cause damage, contamination and/or inconvenience for the user.

These and other aspects of, and advantages with, the present disclosure will become apparent from the following detailed description of the disclosure and from the accompanying drawings.

BRIEF DESCRIPTION OF THE FIGURES

In the following detailed description of the disclosure, reference will be made to the accompanying drawings, of which:

FIG. 8 illustrates a longitudinal cross-section of a medicament delivery device with a pre-filled multi-chamber cartridge or container and a knob having an enlarged cross-section at the distal end as a second embodiment of the medicament delivery device shape.

FIG. 9 illustrates a front view of the medicament delivery device as in shown in FIG. 8.

DETAILED DESCRIPTION

Figure 1:
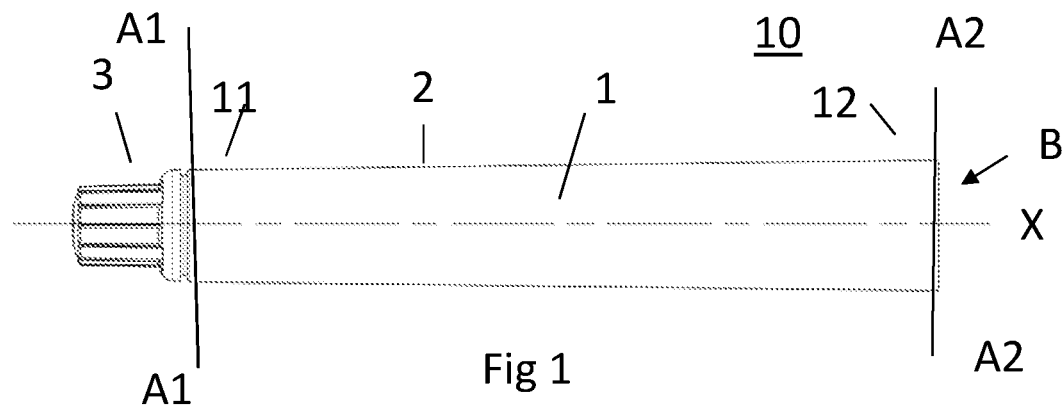
FIG. 1 illustrates an elongated body of the medicament delivery device according to a first aspect of the disclosure, having an enlarged dimension distal end as a first embodiment.

As illustrated in FIG. 1, the medicament deliver device 10 has an elongated body 1 and a longitudinal central axis X. The body 1 has a proximal end 11 and may be provided with a protective cap 3 covering a delivery member (not shown) and a distal end 12 which is formed so that to allow the device 10 to be positioned vertically, with its proximal end 11 upwards, standing on its base distal surface B. The elongated body 1 has a larger cross-sectional area A2 as illustrated by section A2-A2 at its distal end 12 than a corresponding cross-sectional area A1 at a section A1-A1 at its proximal end 11. The cross-sectional area A2 may have different shapes as illustrated in FIG. 2-7, which shapes will be described later.

As illustrated in FIG. 1, the longitudinal body 1 may have an outer housing 2 or an outer shell 2 and a part of this outer housing 2 may form the distal base surface B which is arranged to be perpendicular to the longitudinal axis X and may be provided with anti-slipping properties for enhancing the stability of the device 10 when positioned vertically, as will be explained later.

Figure 17:
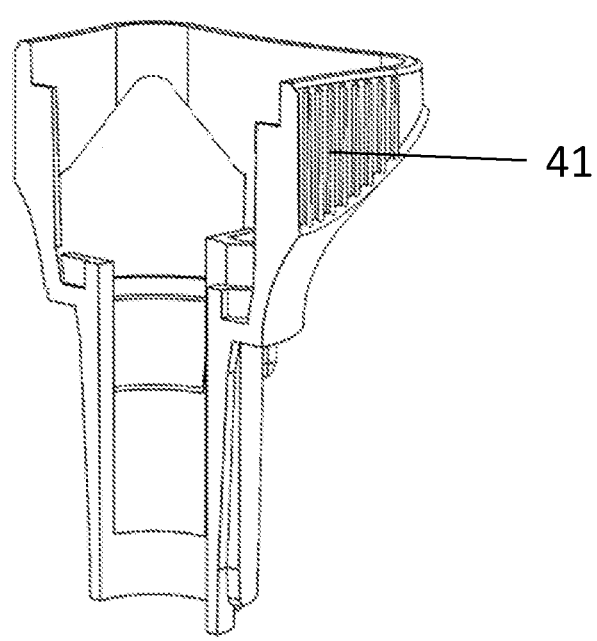
FIG. 17 illustrates a perspective cross-sectional view a section of a dose setting knob serving as a base for the medicament delivery device.
Figure 18:
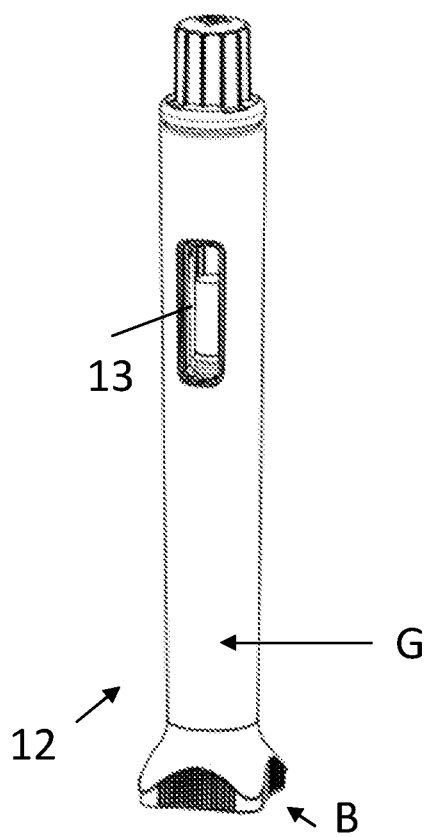
FIG. 18 illustrates a perspective view of the medicament delivery device of FIG. 8 after mixing and prior to priming.

FIG. 8 is a cross-sectional longitudinal view of a second embodiment of the medicament delivery device 10, where the elongated body 1 is formed by the outer housing 2 having a cylindrical shape and a knob 4 having an enlarged dimension of its distal part, and forming the distal surface B. A proximal part of the knob 4 is connected to the cylindrical housing 2. A more detailed cross-sectional view of the knob 4 is also illustrated in FIG. 17, where the base surface B on the distal part is removed. The knob 4 may serve as a dose setting knob 4 or as an activation knob 4. Alternatively, it may comprise an activation button (not shown), e.g. comprised on the base surface B or on a side surface of the knob 4. Alternatively, an activation button (not shown) can be situated on a circumferential surface of the outer housing 2.

Figures 2, 3:
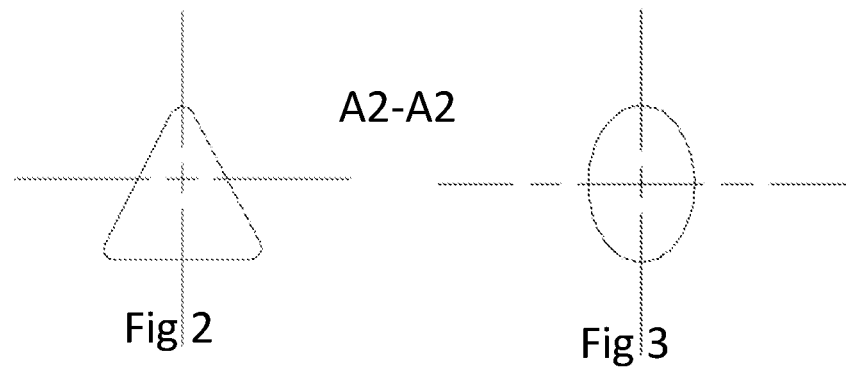
FIG. 2 illustrates a triangular cross-sectional shape of the distal end of the medicament delivery device according to the second aspect of the disclosure.
FIG. 3 illustrates an oval cross-sectional shape of the distal end of the medicament delivery device according to the second aspect of the disclosure.
Figures 4, 5:
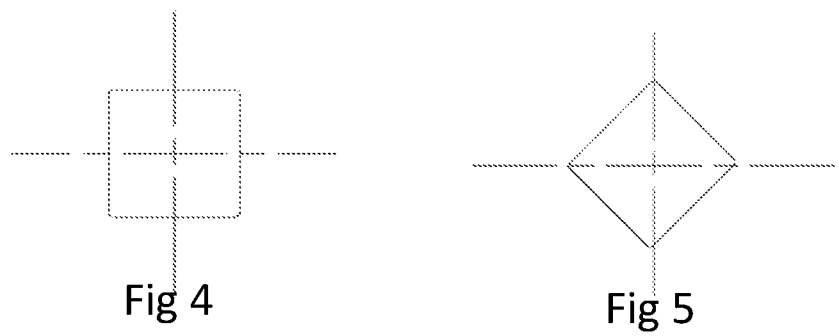
FIG. 4 illustrates a squire cross-sectional shape of the distal end of the medicament delivery device according to the second aspect of the disclosure.
FIG. 5 illustrates a rhombus cross-sectional shape of the distal end of the medicament delivery device according to the second aspect of the disclosure.
Figures 6, 7:
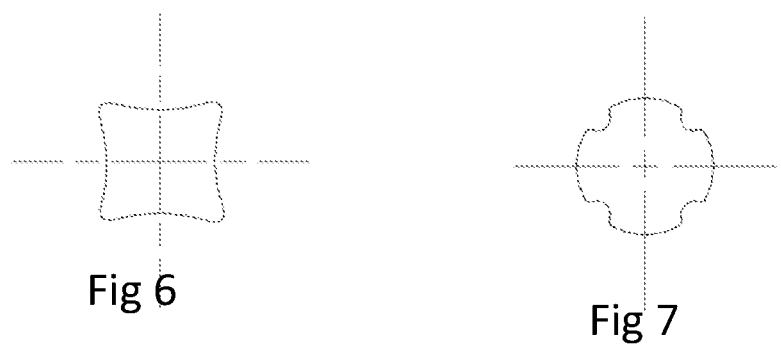
FIG. 6 illustrates a polygonal cross-sectional shape of the distal end of the medicament delivery device according to the second aspect of the disclosure.
FIG. 7 illustrates an irregular circular cross-sectional shapes of the distal end of the medicament delivery device according to the second aspect of the disclosure.

As shown in FIG. 2, the medicament delivery device 10 may be an auto-injector 10 and may comprise a multi-chamber cartridge 7 or container 7" of known design. An active substance is used in a dried or powder form. The dried substance/medicament, e.g. a powder, may be mixed with a liquid diluent L prior to dose administration. The cartridge 7 is usually pre-filled with a medicament M, which is separated from diluent L by a proximal stopper 9 forming a first chamber which first chamber may also include some air A. A second chamber is pre-filled with the diluent L and may also contain some air. The second chamber is closed by a distal stopper 9'. The proximal end of the device 10 is provided with a delivery member. In the illustrated embodiment of an injector, the delivery member is a needle 6, which is also configured with a needle shield arrangement 5. Alternatively, for the inhalers, the delivery member may be a nozzle and/or a spray unit.

The medicament delivery device 10 has a plunger rod 81, which when the device 10 is activated, acts on the distal stopper 9' to move it in the proximal direction.

In FIG. 9, the medicament delivery device 10 is placed vertically and stands on its base surface B at the distal end 12. The device 10 has a monitoring window 13 for monitoring a status of preparations for use. The distal end 12 has the knob 4 which is provided with ribs 41, as also shown in FIG. 17, for enhancing a user's grip and for facilitating the setting of a desired dose and/or for activating the device 10.

Figure 10:
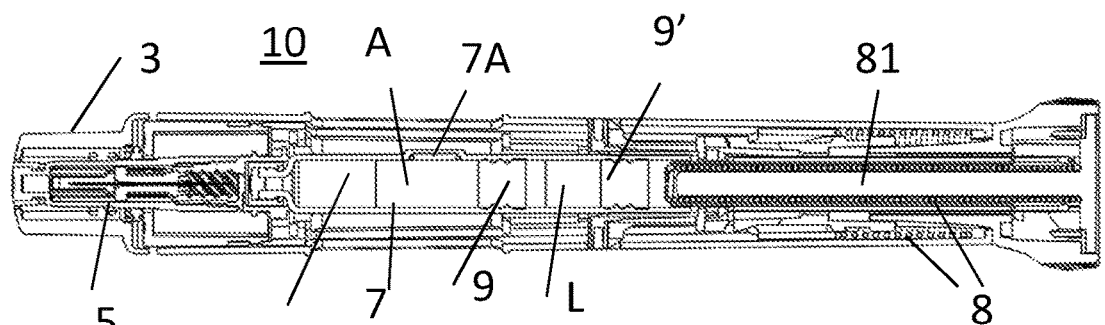
FIG. 10 illustrates a longitudinal frontal view of the embodiment as in FIG. 8 turned 90° of the medicament delivery device according to the disclosure.

FIG. 10 shows a longitudinal cross-section of the medicament delivery device 10 turned 90° around the axis X, as compared to FIG. 8. FIG. 10 illustrates a by-pass channel 7A in a wall of the cartridge 7, which by-pass channel enables the mixing the liquid solvent/diluent L with the medicament M, according to a known process. A drive mechanism 8 drives the plunger rod 81.

FIG. 11-FIG. 16 illustrate sequences of the mixing process of the medicament delivery device 10 with a two-chamber cartridge 7. The device is illustrated horizontally only for illustrative purposes. In practice the process is performed in the vertical, standing, position of the device 10, as illustrated in FIGS. 3, 7, 10 and 11.

Figure 11:
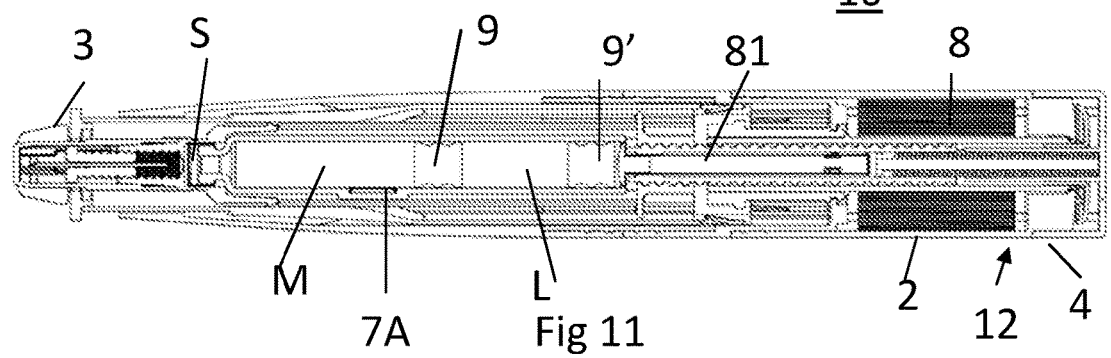
FIG. 11 illustrates a third embodiment of the device at a start of the mixing process of the medicament delivery device, before medicament delivery.

FIG. 11 illustrates a third embodiment of the device 10. The proximal end 11 of the device 10, as illustrated, has a smaller cross-sectional area A1 than the cross-sectional area A2 of the distal end 12. The third embodiment differs from the second embodiment (shown in FIG. 8-10) in that the distal end 12 of the medicament delivery device 10 outer housing 2 has the same general dimensions, or cross-sectional area, as the outer dimension of the knob 4.

Figure 12:
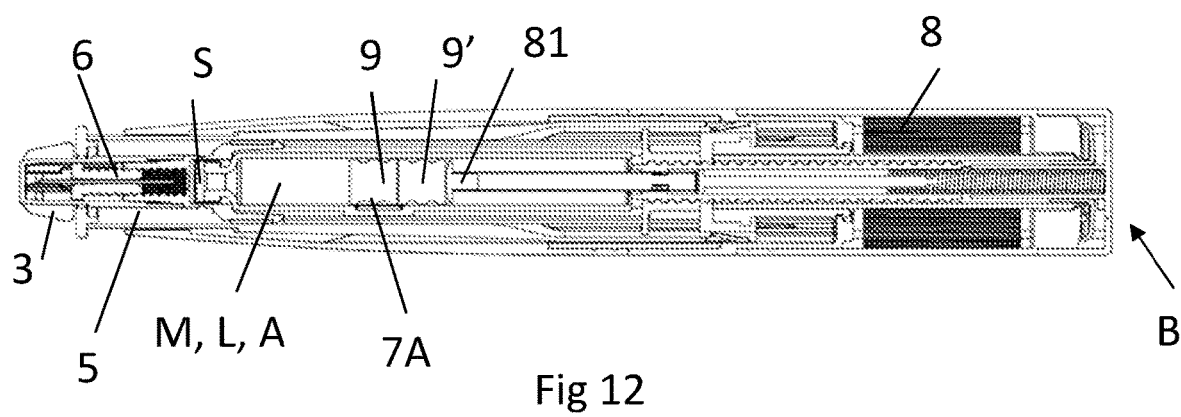
FIG. 12 illustrates a mixing stage.

FIG. 11 illustrates a start of the mixing process of the medicament delivery device 10, before medicament delivery. When the drive mechanism 8 (illustrated as a spring driven mechanism) is activated, the plunger rod 81 is actuated to move proximally so that the distal stopper 9' is moved by the plunger rod 81 in the proximal direction, exerting a pressure on the liquid L solvent in the pre-filled in the cartridge 7. The cartridge 7 is sealed at its proximal end by a septum S. As liquid is incompressible, the proximal stopper 9 will also be moved in the proximal direction by the pressure exerted on the liquid volume and pushed by the plunger rod 81 until it passes the by-pass channel 7A, as illustrated in FIG. 12. The liquid diluent L is thereby able to escape via the by-pass channel 7A into the first chamber containing the medicament M and air A for mixing the medicament with the diluent L. Thus, the first chamber consequently contains a mixture of the medicament M, liquid L and air A. The mixture, or reconstituted medicament, may sometimes form foam depending on the constituent components and/or on the speed of mixing. At the end of the mixing stage, the distal stopper 9' contacts the proximal stopper 9. Further movement of the plunger rod 81 will move both stoppers 9, 9' together.

As explained previously, air bubbles A may accidentally expel a portion of the reconstituted medicament mixture prior to dose delivery thus changing the actual dose of the medicament ready to be delivered to the user. If the reconstituted medicament is of a higher viscosity, some time may be required to let all air bubbles A escape. The device 10 may therefore need to be kept vertical during this process.

Therefore, it is an advantage if the medicament delivery device 10 may be placed on its base surface B at its distal end 12, so that the user does not need to hold it during the priming process.

Figure 21:
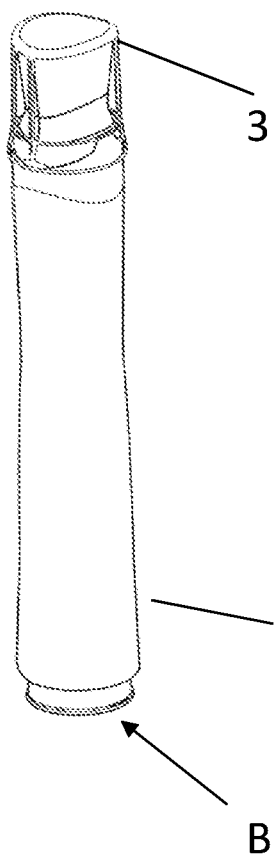
FIG. 21 illustrates a vertical positioning of the device according to the disclosure.
Figure 22:
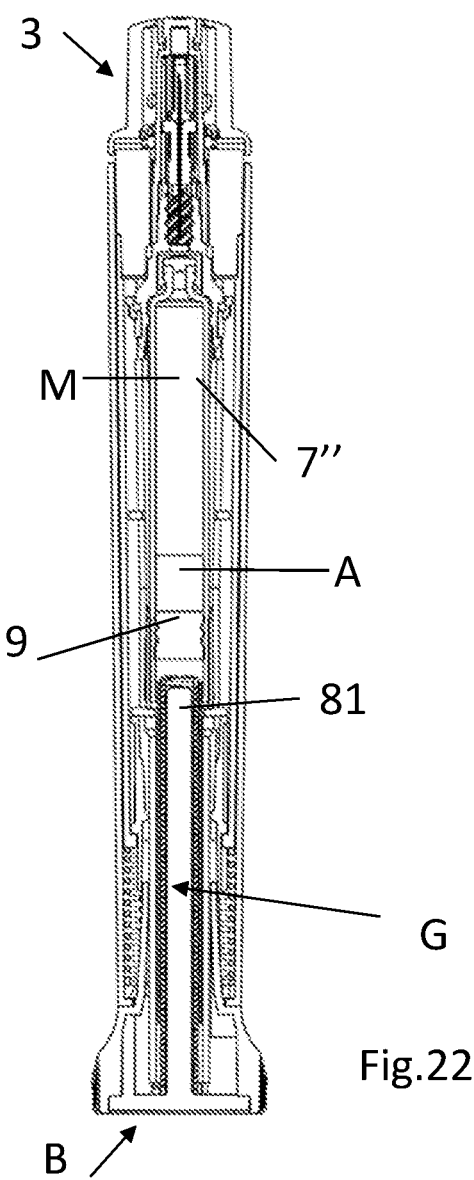
FIG. 22 illustrates an inhaler as a medicament delivery device.

The medicament delivery device 10 is able to stand steadily on its base surface B. Activation of the drive mechanism 8, or alternatively, a removal of the cap 3 by the user may activate the priming process. In the illustrated embodiment, the cartridge 7 with the septum S and a separate movable needle 6 are used. The needle 6 is able to move distally so as to penetrate the septum S and allow air bubbles A to evacuate the first chamber containing the reconstituted medicament. Alternatively, a pre-filled syringe 7', with a medicament M in liquid form, which syringe has an attached needle (not shown), or a single chamber pre-filled container 7" may also contain an amount of air A as illustrated in FIG. 22. Therefore, such containers may require priming prior to administration of the medicament. The same applies to inhalers, as illustrated in FIG. 21.

The drive mechanism 8 includes the plunger rod 81 and usually involves either drive spring or the other mechanical driving elements. Components of metal are heavier than most plastic details constituting the proximal part 11 of the delivery device 10. The drive mechanism 8 is located in a distal part of the device 10. Therefore a centre of gravity G of the entire medicament delivery device 10 will also be located closer to the distal end 12 than to the proximal end. Such placement of the centre of gravity G enhances stability in the vertical position of the medicament delivery device 10, when standing on the distal base surface B. Such placement of the centre of gravity G may be in addition to, or instead of, providing the enlarged cross-sectional area A2 of the distal end 12 (in relation to the proximal end 11 cross-sectional area A1). The surface B is substantially perpendicular to the axis X.

After priming, the medicament is ready to be delivered to the user according to any conventional steps known in the art.

Figure 13:
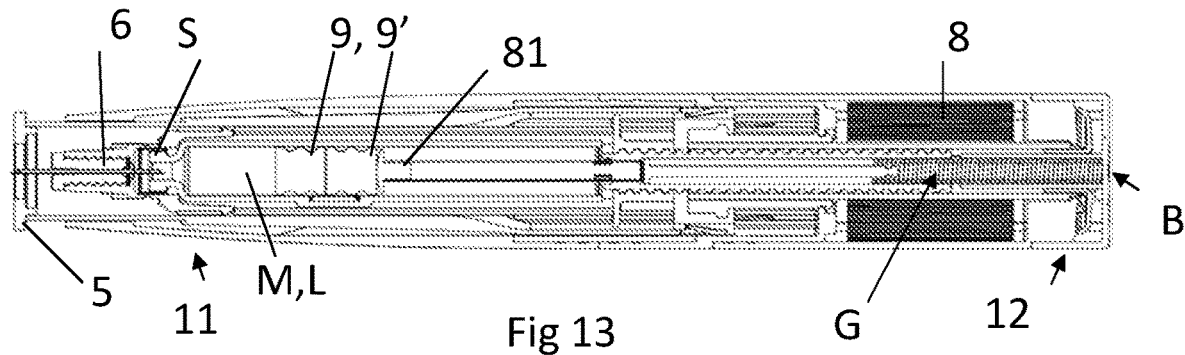
FIG. 13 illustrates another embodiment of the delivery device.
Figure 14:
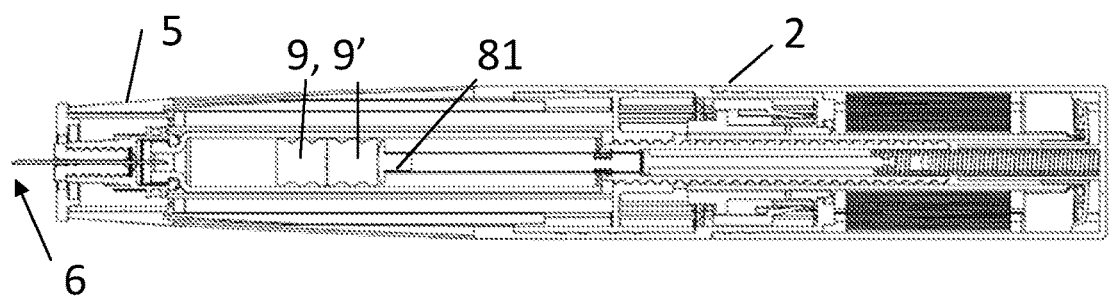
FIG. 14 illustrates still another embodiment of the delivery device.
Figure 15:
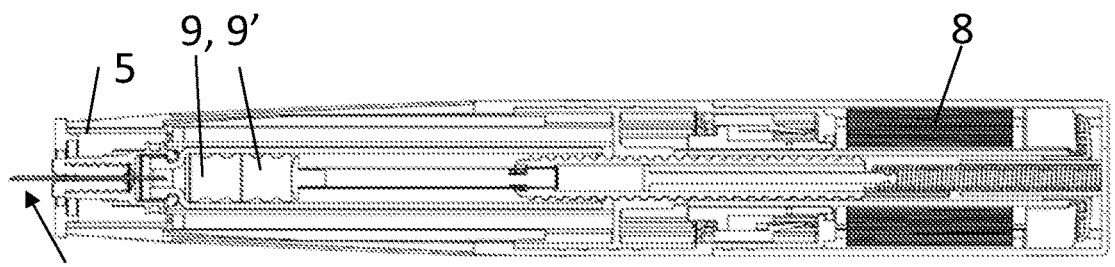
FIG. 15 illustrates a fourth embodiment of the medicament delivery device at the end of the injection.
Figure 16:
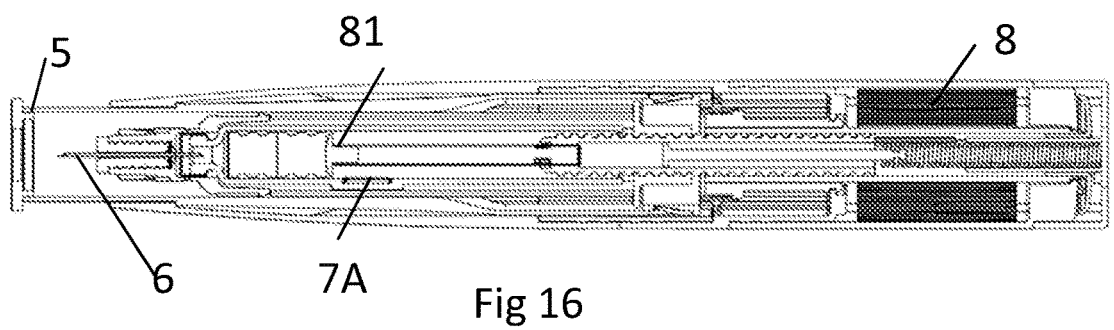
FIG. 16 illustrates the last sequence in the function of the multi chamber medicament delivery device of a third embodiment of the medicament delivery device shape.

The third embodiment of the shape of the medicament delivery device 10 is illustrated in FIG. 11-16. As mentioned previously, the medicament delivery device 10 has the outer housing 2 of the same dimension as the knob 4 being connected to the housing 2, while the outer shape of the knob 4 may be similar or different from the outer shape of the outer housing 2, depending on the desired features of the knob 4. Alternatively, the shape of either the knob 4 of the third embodiment as shown in FIG. 13 or the shape of the outer housing 2 of a fourth embodiment, illustrated in FIGS. 14-15, may have one of the shapes illustrated in FIGS. 2-7.

It is not necessary for the distal end 12 and the proximal end 11 of the outer housing 2 to have the same shape and/or the same dimensions. However, at least one of the outer housing 2 ends 11, 12 should be configured with a non-circular shape, such that the non-circular shape will prevent the device 10 from rolling in a horizontal position on the surface. The non-circular shape may be oval, rectangular, polygonal or an irregular shape of the outer housing 2. Variant shapes having cut-outs from an otherwise circular shape may also prevent rolling of the device 10 in the horizontal position. The non-circular shape of the distal end 12, may smoothly transform along the longitudinal axis X into the outer shape of the housing 2 at its proximal end 11, having the smaller cross-sectional area A1.

Figure 19:
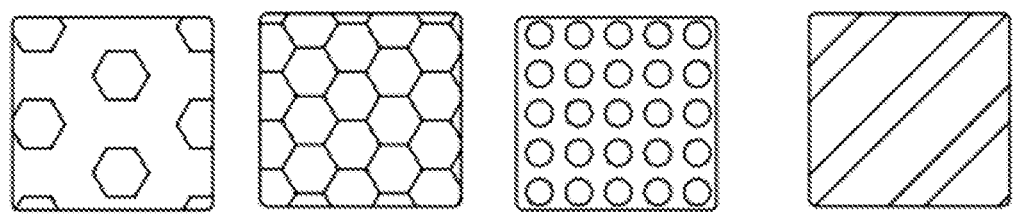
FIG. 19 illustrates a number of possible structural patterns of a rear base surface for enhancing its friction in relation to a supporting surface on which the medicament delivery device is to be placed vertically.
Figure 20:
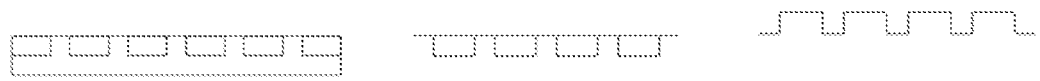
FIG. 20 illustrates a number of possible cross-sections of the patterns in FIG. 8 for enhancing the friction of the distal base surface of the medicament delivery device in a vertical, standing position.

The base surface B of the distal end 12 of the elongated body 1 of the medicament delivery device 10 should be generally flat and substantially orthogonal to the longitudinal axis X of the device 10. Besides the enlarged distal end 12 of the device 10, or the distal part of the knob 4, and the center of gravity G of the device 10 situated in the distal part of the medicament delivery device 10, the base surface B may be provided with an anti-slipping arrangement for increased friction against the supporting surface on which the device 10 is to be placed for priming. The base surface B of the device 10 may be provided with a special surface of a particular material, e.g. a piece of a rubber, or any coarse material known for the purpose of having an increased friction. The surface may also be manufacture with a surface structure to increase friction. The high-friction surface/ material/structure may alternatively be attached to the base surface B, such as by gluing. Another alternative is to mold the base surface B to have any of a wide range of patterns, or structures, for increasing the surface coarseness, such as illustrated in FIG. 19, in the form of regular or irregular grooves, circles or polygons, and formed as plurality of indentations and/or protrusions on the base surface B as illustrated in FIG. 20. The coarseness and/or the patterns and/or materials for increasing friction between the base surface B of the medicament delivery device 10 and the supporting surface, e.g. a surface of a table or a desk, will further improve the stability if the elongated body 1 in the vertical position.

It is to be understood that the embodiments described above and shown in the drawings are to be regarded only as a non-limiting example of the disclosure that may be modified in many ways within the scope of the patent claims.

The invention claimed is:

1. A medicament delivery device, comprising:
an elongated body formed by an outer housing shell and a knob, wherein the elongated body includes a longitudinal axis, a proximal end comprising a dose delivery site, and a distal end pointing away from the dose delivery site and provided with a distal surface, wherein the distal surface is formed by the knob, wherein the knob is fixed longitudinally relative to the outer housing shell, wherein the distal end and the distal surface are arranged and configured such that the elongated body of the medicament delivery device will stand steadily on the distal surface in a substantially vertical position, wherein a cross-sectional area at the proximal end perpendicular to the longitudinal axis is smaller than a cross-sectional area at the distal end perpendicular to the longitudinal axis, and wherein the cross-sectional area at the distal end has a non-circular shape to thereby prevent a rolling of the medicament delivery device when being in a substantially horizontal position; and
a needle configured to extend proximal to the proximal end of the elongated body.

2. The medicament delivery device according to claim 1, wherein the distal surface of the elongated body is flat.

3. The medicament delivery device according to claim 1, wherein the distal surface has an anti-slipping arrangement.

4. The medicament delivery device according to claim 3, wherein the anti-slipping arrangement comprises at least one of an anti-slipping material and an anti-slipping surface profile to ensure a stability of the medicament delivery device in the substantially vertical position.

5. The medicament delivery device according to claim 1, wherein the cross-sectional area at the proximal end and the cross-sectional area at the distal end of the elongated body have different circumferential shapes.

6. The medicament delivery device according to claim 1, wherein the knob is one of a dose setting knob, and a device activating knob, a mixing knob, an unlocking knob and a charging connector knob.

7. The medicament delivery device according to claim 1, wherein the medicament delivery device further comprises one of a multi-chamber cartridge, a syringe and a single chamber container with a medicament.

8. The medicament delivery device according to claim 1, wherein a distance along the longitudinal axis from a center of gravity of the medicament delivery device to the distal end is shorter than to the proximal end of the elongated body.

9. The medicament delivery device according to claim 1, wherein the medicament delivery device is one of an automatic or a manual injection device.

10. A medicament delivery device, comprising:
an elongated body formed by an outer housing shell and a knob, wherein the elongated body includes a longitudinal axis, a proximal end comprising a dose delivery site and comprising a proximal end cross-sectional area, a distal end pointing away from the dose delivery site and comprising a distal end cross-sectional area and providing a flat distal surface, wherein the flat distal surface is formed by the knob, wherein the knob is fixed longitudinally relative to the outer housing shell, wherein the distal end cross-sectional area is configured with a shape and size such that the elongated body will stand steadily on the flat distal surface in a substantially vertical position, wherein the proximal and distal end cross-sectional areas are perpendicular to the longitudinal axis, wherein the proximal end cross-sectional area is smaller than the distal end cross-sectional area, and wherein the distal end cross-sectional area has a non-circular shape to thereby prevent a rolling of the medicament delivery device when being in a substantially horizontal position; and
a needle configured to extend proximal to the proximal end of the elongated body.

11. The medicament delivery device according to claim 10, wherein the flat distal surface has an anti-slipping arrangement.

12. The medicament delivery device according to claim 11, wherein a distance along the longitudinal axis from a center of gravity of the medicament delivery device to the flat distal surface is shorter than to the proximal end of the elongated body.

13. The medicament delivery device according to claim 10, wherein the proximal end cross-sectional area has a first circumferential shape and the flat distal surface has a second circumferential shape, where the first and second circumferential shapes are different.

* * * * *